United States Patent [19]

Inoue et al.

[11] 4,306,024
[45] Dec. 15, 1981

[54] PROCESS FOR CULTIVATION OF HEMOLYTIC *STREPTOCOCCUS PYOGENES*

[75] Inventors: Shintaro Inoue; Mikio Sotomura; Hiroshi Tanaka, Setsu; Seiichi Iwamoto, Osaka; Norimasa Takamatsu, Nara; Akira Suzuki, Tondabayashi; Isamu Utsumi, Kyoto, all of Japan

[73] Assignee: Kanebo Ltd., Tokyo, Japan

[21] Appl. No.: 140,864

[22] Filed: Apr. 16, 1980

[51] Int. Cl.$^3$ .................. C12N 1/20; C12N 1/38; C12R 1/46

[52] U.S. Cl. ................. 435/170; 435/68; 435/244; 435/253; 435/885

[58] Field of Search .......... 435/68, 91, 170, 244, 435/248, 249, 253, 885

[56] References Cited

U.S. PATENT DOCUMENTS 3,477,914 11/1969 Okamoto et al. ............. 435/885 X
3,627,644 12/1971 Okamoto et al. ............. 435/885 X

FOREIGN PATENT DOCUMENTS 1157947 7/1969 United Kingdom .

OTHER PUBLICATIONS

Okamoto et al., *Gann*, 55, 225–232 (1964).
Okamoto et al., *Japan J. Exp. Med.*, 34(3), 109–118 (1964).
Ohtsuki, Annual Reports of the Research Institute for Cancer, Kanazawa University, vol. 1, 141–153 (1967).

*Primary Examiner*—Esther M. Kepplinger
*Attorney, Agent, or Firm*—Wenderoth, Lind & Ponack

[57] ABSTRACT

A process for cultivation of *Streptococcus pyogenes* comprising cultivating *Streptococcus pyogenes* in a culture medium for multiplication of bacterial cells having an anti-tumor activity, characterized by (A) using the culture medium containing fermentable carbon sources and (B) maintaining pH of the culture medium at 5.6 or more during the course of cultivation.

9 Claims, No Drawings

PROCESS FOR CULTIVATION OF HEMOLYTIC *STREPTOCOCCUS PYOGENES*

The present invention relates to a process for cultivation of hemolytic *Streptococcus pyogenes* (hereinafter called *St. pyogenes* for short) and more particularly, to a process for cultivation of *St. pyogenes* by which to obtain bacterial cells having a high Streptolysin-S (hereinafter called SLS for short)-producing ability and anti-tumor activity in high yield. *St. pyogenes* are pathogenic bacteria of erysipelas, septicemia, puerperal fever and other various diseases, but some parts of *St. pyogenes* are known to have the anti-tumor activity from old, and in recent years they have become used clinically as anti-cancer agents. The anti-tumor activity of *St. pyogenes* has a close relation with its SLS-producing ability, and even among *St. pyogenes* present in the natural world it is only those strains having the SLS-producing ability that have the anti-tumor activity. It is also known that even with *St. pyogenes* having the SLS-producing ability the anti-tumor activity will be simultaneously lost if they are cultivated in such conditions as to lose the SLS-producing ability. This example is well investigated in the case of cultivating *St. pyogenes* in the presence of glucose and it is known that if glucose is added even in a small amount to the culture medium, the SLS-producing ability is rapidly lowered, that if the amount of glucose added reaches 0.3% or more the SLS-producing ability is nearly completely lost entailing the simultaneous loss of the anti-tumor activity and that if not only glucose but also lactose, fructose, mannose or glyceraldehyde is added to the culture medium, the SLS-producing ability of the bacterial cells is inhibited (refer to H. Okamoto et al. GANN, Vol. 55, p. 225-232; June 1964; H. Okamoto et al. Japan. J. Exp. Med., Vol. 34, No. 3, p. 109-118, 1964 and H. Ohtsuki Annual Reports of the Research Institute for Cancer, Kanazawa University, Vol. 1, p. 141-153, 1967).

Studies made by the instant inventors confirm the fact that if fermentable carbon sources, such as glucose, are added to culture media for cultivation of *St. pyogenes*, the SLS-producing ability of the bacterial cells is markedly lowered or lost and the anti-tumor activity of the bacterial cells as well is lowered or lost.

For the above-described reasons one was forced to use culture media not containing the said carbon sources in order to obtain bacterial cells having high anti-tumor activity (See U.S. Pat. No. 3,477,914).

Hence, as the process of cultivation for obtaining bacterial cells having high anti-tumor activity, proposals have thenceforth been made for those involving the using of yeast extract media not containing fermentable carbon sources and it has come to be disclosed that by using yeast extract as a culture medium there could be obtained bacterial cells which are comparatively high in SLS-producing ability (See British Pat. No. 1,157,947), but this process is not satisfactory in that the cell growth is much inferior.

The present invention is designed to provide a process for cultivation of *St. pyogenes* by which to obtain bacterial cells of *St. pyogenes* having a high SLS-producing ability and a high anti-tumor activity in high yield.

Another purpose of the present invention is to provide a cultivation process for obtaining bacterial cells having a high SLS-producing ability in high yield despite the containing of fermentable carbon sources in the culture medium which were conventionally conceived to constitute the factor of markedly lowering or losing the SLS-producing ability.

Still other purposes and merits of the present invention will be clarified from explanations which follow.

The present invention will be explained as follows:

In the present invention the said purposes and merits were found to be achieved by (A) using a culture medium containing the fermentable carbon sources and (B) maintaining the pH of the culture medium at 5.6 or more during the course of cultivation in a process of cultivating *St. pyogenes* in a culture medium for multiplication of the bacterial cells.

Considerably detailed information of processes for cultivating *St. pyogenes* in culture media for multiplication of the bacterial cells having the anti-tumor activity, for example of culture media, cultivating conditions and so forth used on that occasion, are already known from H. Okamoto et al. above-mentioned Reports and above cited U.S. Patent and British Patent.

H. Okamoto et al. recommend using culture media which do not contain fermentable carbon sources (e.g. glucose) and in particular, yeast extract culture media which are known to contain no such fermentable carbon sources.

In the present invention, on the other hand, not only culture media containing fermentable carbon sources, but also those culture media not containing fermentable carbon sources but to which fermentable carbon sources are added, are available and this is one characteristic feature of the present invention.

In the present invention it is possible to use, as the basal culture media, a very wide range of media, such as natural media, such as nutrient broth, Todd-Hewitt broth, a casein soy peptone broth, pumpkin extract broth, yeast extract broth, soy peptone broth and so on, and semi-synthetic media. By the basal culture media referred to here are meant culture media capable of growing *St. pyogenes* irrespective of whether or not they have the SLS-producing ability. In the case, as hereinafter-described, of basal culture media primarily containing fermentable carbon sources they can be used as such or by addition of appropriate amounts of fermentable carbon sources as the culture media of the present invention.

Any carbon sources which *St. pyogenes* can ferment will suffice for the carbon sources capable of adding to the basal culture medium. Preferred are saccharides or their derivatives such as glucose, mannose, fructose, lactose, sucrose, maltose, glyceraldehyde, trehalose, dextrin, soluble starch, molasses and so on. Among the saccharides, monosaccharides and disaccharides, are particularly preferred. Glucose as the monosaccharide and sucrose as the disaccharide are advantageously used.

Any culture media, which are able to grow *St. pyogenes* and contain such fermentable carbon sources are available for the culture media of the present invention.

Consequently, culture media primarily containing some fermentable carbon sources, such as the said Todd-Hewitt broth (containing about 0.2% glucose), casein soy peptone broth (containing about 0.25% glucose), pumpkin extract broth (containing about 0.1% glucose), soy peptone broth (containing about 0.4% reducing sugar) and so on, could be used either as such or by the further addition of the said fermentable carbon sources. Even in the case, however, of those culture media primarily containing fermentable carbon sources preferably at least 0.1% of the carbon sources should be positively added. By so doing the bacterial cells of *St. pyogenes* having good SLS-producing ability could be multiplied in higher yield. In the case of culture media not containing fermentable carbon sources, such as the said nutrient broth and yeast extract broth, it is required to add fermentable carbon sources to them for use as the culture media of the present invention.

Whether fermentable carbon sources are added to the culture media or not, the culture media of the present invention should preferably contain fermentable carbon sources in the amount of 0.1-5% (weight/volume), more preferably 0.1-2% (weight/volume) and most preferably 0.3-2% (weight/volume). In the case of glucose, for instance, it is 0.1-3% (weight/volume) and particularly 0.3-2% (weight/volume).

The "weight/volume" referred to here means weight of fermentable carbon sources/volume of culture medium and the concentration (%) of the carbon sources in the culture medium will all be based on this definition hereinafter.

The case being so, whether the basal media primarily contain carbon sources for *St. pyogenes* to ferment or not, those are advantageously used which were prepared by adding the carbon sources in such a manner as to have the concentration of the carbon sources in the culture medium falling within the said range.

In the present invention, particularly preferred culture media are (1) yeast extract broth in which 0.1-5%, preferably 0.3-2%, of fermentable carbon sources, particularly glucose or sucrose, were added, or (2) soy peptone broth in which 0.1-5%, preferably 0.1-1.5%, of fermentable carbon sources, particularly glucose or sucrose, were added.

RNA or RNase-core, if necessary, could be added to the culture media of the present invention.

The initial pH of the culture medium, which is able to grow *St. pyogenes* and contains fermentable carbon sources in the said concentrations, is usually about 7.1-7.4, but when *St. pyogenes* are cultivated in such a culture medium, the pH of the culture medium is lowered by degrees during the continuance of cultivation and in the stage where the bacterial cells of *St. pyogenes* are considerably multiplied, the pH of the culture medium is lowered to nearly 5.3 or less and usually 5.2 or less. It is not rare that the pH is lowered further than 5.0 depending upon the culture medium used.

For its cause it is assumed by the instant inventors that *St. pyogenes* ferment the carbon sources in the culture media whereby certain kinds of organic acids are caused to occur in the culture media.

The instant inventors closely investigated a relationship between the changing of the pH of the culture medium during the continuance of cultivation and the SLS-producing ability of the bacterial cells of *St. pyogenes* which were multiplied in a culture medium containing such fermentable carbon sources. In consequence, it was found that if the pH of the culture medium was lower than 5.6, in general, the SLS-producing ability of the bacterial cells would be rapidly lowered and that if *St. pyogenes* were to be continuously cultivated while maintaining the pH of the culture medium at 5.6 or more, surprisingly enough, the bacterial cells high in SLS-producing ability would be multiplied in very high yield.

Conventionally, it is known that if maltose is used as fermentable carbon source, the SLS-producing ability of the bacterial cell will be sustained to some extent the fact that the pH of the culture medium is lowered to 5 or thereabout (H. Ohtsuki Annual Reports of Research Institute for Cancer, Kanazawa University, Vol. 1, p. 141-153, 1967). Hence, no one attracted his attention to any attempts to improve the SLS-producing ability of the bacterial cell by controlling the pH of the culture medium during the continuance of cultivation.

According to the present invention, in the case of using fermentable carbon sources other than maltose, it is indispensable to hold the pH of the culture medium at 5.6 or more particularly at 6 or more during the continuance of the cultivation for the multiplication of the bacterial cells of *St. pyogenes* high in SLS-producing ability. And, even in the case of using maltose as the carbon source, by controlling the pH so as to fall within the said range, the bacterial cells higher in SLS-producing ability could be obtained in higher yield.

According to the present invention, cultivation is effected by inoculating *St. pyogenes* to the fermentable carbon source-containing or -added culture medium and while maintaining the pH of the culture medium at 5.6 or more, preferably at 5.6-7.5 and more preferably at 6-7. A temperature of 30°-40° C. will suffice for the culture temperatures, but 35°-37° C. is preferred. The cultivating time varies depending upon the kind of the culture medium, the amount of fermentable carbon sources, inoculum size and so forth, but it is 8-72 hours long and bacterial cells meeting the requirement for either of cell growth, SLS-producing ability and anti-tumor activity can usually be obtained in 12-40 hours.

Even in the range of said cultivating time the cultivating time is preferably prolonged as the concentration of the carbon source in the culture medium becomes greater.

For the pH adjustment of the culture medium there are employed known methods, such as a method involving the using of buffer solution, a neutralization method and so on. For one thing, phosphate buffer solution (pH 7.0-7.5) is added in such a manner as to reach 50-300 mM, preferably 100-200 mM, in the concentration in the culture medium. Further, cultivation is effected by adding dropwise an aqueous solution of caustic soda, potassium hydroxide, ammonia, basic amino acid or the like (aqueous solution of hydrochloric acid, sulphuric acid, phosphoric acid, acidic amino acid or the like as the case may be) with agitation at such low rate as 100-500 rpm, while adjusting the pH of the culture medium.

By centrifuging the culture solution so cultivated while cooling, the intended bacterial cells of *St. pyogenes* are collected. They are excellent both in the cell growth and in anti-tumor activity.

The present invention will be explained in more detail with reference to working examples as follows. In this connection, in the examples, unless otherwise specified, "%" means "% by weight/volume" and cell growth, SLS-producing ability and in vivo anti-tumor activity were measured by following the below-mentioned procedures.

[Cell growth ($OD_{660}$)]

Bacterial cells obtained by centrifuging a predetermined amount of culture solution were washed twice with physiological saline, then the bacterial cells were diluted with the said saline in such a manner as to reach 0.1–0.2 in absorbance at 660 nm ($OD_{660}$). $OD_{660}$ of the diluted solution was measured and $OD_{660}$ of the culture solution was calculated by multiplying this value by dilution ratio.

[SLS-producing ability]

5 ml each of culture solutions of appropriate cultivating hours after inoculation in the respective Examples were taken respectively into test tubes, cooled in ice, cold centrifuged (3500 rpm × 10 minutes), then washed with Bernheimer's basal medium (medium comprising 675 mg of maltose, 6 ml of 20% aqueous solution of potassium dihydrogen phosphate adjusted to pH 7.0 with sodium hydroxide and 12 ml of 2% aqueous magnesium sulphate heptahydrate and 66 ml of distilled water, hereinafter called BBM for short) and suspended in 2 ml of fresh BBM. Added to this so as to reach 0.06% was RNase-core (prepared from pancreatic RNase digest of Yeast-Sodium Ribonucleate "Merck") and it was incubated at 37° C. for 60 minutes, centrifuged at 3500 r.p.m. for 10 minutes at low temperature and 1 ml of the supernatant was taken and diluted with cold buffer solution (of which the 1 liter contained 7.4 g of sodium chloride, 3.17 g of potassium dihydrogen phosphate and 3.59 g of disodium hydrogen phosphate dodecahydrate, pH 6.5) by two-fold dilution method. Added to 1 ml each of the diluted solutions was 1 ml of rabbit erythrocyte (which had been washed several times with the buffer solution and adjusted with the buffer solution so as to reach 3% (V/V) in the concentration) and it was held at 37° C. for 60 minutes. The dilution ratio of the original BBM solution at which to cause 50% hemolysis was measured and multiplied by 0.4. Hemolytic unit (HU) of the culture solution was indicated by the maximum value of those of specimens for the time course of cultivation.

[In vivo anti-tumor activity]

The culture solution in each of Examples was taken in the amount of 250 ml, cold centrifuged, washed twice with the cold physiological saline, then suspended in cold BBM solution and so adjusted as to reach 10.0 in absorbance at 660 nm ($OD_{660}$). Solution prepared by dissolving potassium salt of penicillin G in 200,000 units in 1.25 ml of physiological saline was added to the BBM solution by 1/5 the amount of it and was held at 37° C. for 20 minutes and then at 45° C. for another 30 minutes and poured for every 1 ml into sterilized vials and lyophilized (5 mg dry cells/vial).

The lyophilyzed preparation so obtained was suspended in 5 ml of physiological saline and it was intraperitoneally administered for every 0.2 ml for 4 successive days to mice which had been intraperitoneally inoculated with $10^6$ cells of Ehrlich ascite carcinoma on the previous day (one group consisting of 5 mice, ddY female mice, about 5 weeks old). As control, likewise mice were intraperitoneally administered with 0.2 ml of physiological saline. The anti-tumor activity was indicated by the number of mice surviving 20 days and 30 days after inoculation of Ehrlich ascites carcinoma.

In the instant tests the number of mice surviving 20 days and 30 days after inoculation was zero in either case with mice of control groups.

EXAMPLE 1

[Basal culture medium (5% yeast extract broth)]

50 g of yeast extract (Oriental Yeast Co., Ltd.) was dissolved in 500 ml of distilled water and after adjusting to pH 7.2 to 7.4 it was boiled at 100° C. for one hour, cooled with water, then precipitates were filtered off, the filtrate was readjusted to pH 7.2–7.4 and boiled once again at 100° C. for 30 minutes. After that, it was cooled in water and filtered. Distilled water was added to the filtrate to make 1000 ml and it was sterilized at 121° C. for 20 minutes to make the basal medium.

(Process of the present invention)

To 500 ml of the said basal culture medium (in 1500 ml jar fermenter) was added sterilized glucose solution in such a manner as to reach 0.4% in glucose content based on the total amount of the culture solution and was inoculated 25 ml (5% V/V) of culture solution of St. pyogenes ATCC 21060 cultivated in advance in the nutrient broth (Kyokuto Seiyaku, Ltd.). During the course of cultivation 5N-aqueous caustic soda solution (sterilized) was added dropwise so as to maintain pH at 6.5 by means of pH controller and it was cultivated at 37° C. for 20 hours with agitation at 170 rpm.

(Control A)

To the same basal culture medium as used in Example 1 was likewise added glucose solution and was likewise inoculated culture solution of St. pyogenes. And it was cultivated under the same conditions as in Example 1 except for not controlling the pH of the culture medium.

(Control B)

The same basal culture medium as used in Example 1 was likewise inoculated, but without adding the glucose solution and without controlling the pH of the culture medium it was subjected to statical cultivation at 37° C. for 20 hours.

The cell growth, SLS-producing ability and in vivo anti-tumor activity were measured of the respective culture solutions and Table 1 below shows results obtained.

TABLE 1

| | | | | | | Anti-tumor activity (Number of mice surviving / Number of mice tested) | |
|---|---|---|---|---|---|---|---|
| Experiments | Carbon source (concentration %) | PH control (PH) | Cell growth ($OD_{660}$) [ratio] | SLS-producing ability per unit culture medium (HU/ml) [ratio] | SLS-producing ability per unit cell concentration (HU/$OD_{660}$) [ratio] | After 20 days | After 30 days |
| Example 1 | glucose (0.4) | do (6.5) | 2.3 (2.6) | 570 (2.7) | 248 (1.03) | 5/5 | 5/5 |
| Control A | glucose (0.4) | do not (—)* | 1.2 (1.3) | <4 <0.02 | <4 <0.02 | 0/5 | 0/5 |
| Control B | — | do not | 0.89 | 214 | 240 | 5/5 | 5/5 |

TABLE 1-continued

| | Conditions and Results | | | | | | |
|---|---|---|---|---|---|---|---|
| | | | | | | Anti-tumor activity (Number of mice surviving / Number of mice tested) | |
| Experiments | Carbon source (concentration %) | PH control (PH) | Cell growth (OD$_{660}$) [ratio] | SLS-producing ability per unit culture medium (HU/ml) [ratio] | SLS-producing ability per unit cell concentration (HU/OD$_{660}$) [ratio] | After 20 days | After 30 days |
| | (—) | (—)* | (1.0) | (1.0) | (1.0) | | |

(NOTE)
(i) In all experiments St. pyogenes ATCC 21060 was used for the strain and yeast extract broth was used for the basal culture medium.
(ii) *The final pH of the culture medium in Control A and Control B were 5.2 and 6.6 respectively.

As Table 1 shows, the cells obtained by the process of the present invention (Example 1) is almost the same in the SLS-producing ability per unit cell concentration as well as in the anti-tumor activity as that obtained by the conventional statical cultivation (Control B) and in addition, the cell growth is as high as about 2.6 times that of the latter one and culture efficiency is drastically improved.

In the case, on the other hand, of the cells obtained by adding glucose but not conducting the pH control (Control A), true, some increase is recognized in the cell growth, but the SLS-producing ability is markedly lowered and the anti-tumor activity is lost nearly completely.

EXAMPLES 2, 3, 4

By similar cultivating as in Example 1 except that St. pyogenes ATCC 21059 (Example 2), St pyogenes IID S-43 (Example 3) and St. pyogenes IID T-3 (Example 4) were substituted for St. pyogenes ATCC 21060 of Example 1 there were obtained results as shown in Table 2.

In the respective Controls C, D, E, cultivation was effected by following the procedure of Control B of Example 1 except that they differed in the bacteria used.

TABLE 2

| | | | | | | | Conditions and Results | |
|---|---|---|---|---|---|---|---|---|
| | | | | | | | Anti-tumor activity (Number of mice surviving / Number of mice tested) | |
| Experiments | Strain (St. pyogenes) | Carbon source (concentration %) | PH control (PH) | Cell growth (OD$_{660}$) (ratio) | SLS-producing ability per culture medium (HU/ml) (ratio) | SLS-producing ability per unit cell concentration (HU/OD$_{660}$) (ratio) | After 20 days | After 30 days |
| Example 2 | ATCC 21059 | glucose (0.4) | do (6.5) | 2.4 (2.6) | 672 (3.7) | 280 (1.4) | 5/5 | 5/5 |
| Control C | ATCC 21059 | — (—) | do not | 0.91 (1.0) | 184 (1.0) | 202 (1.0) | 5/5 | 5/5 |
| Example 3 | IID S-43 | glucose (0.4) | do (6.5) | 2.3 (2.6) | 437 (2.2) | 190 (0.86) | 5/5 | 5/5 |
| Control D | IID S-43 | — (—) | do not | 0.88 (1.0) | 195 (1.0) | 222 (1.0) | 5/5 | 5/5 |
| Example 4 | IID T-3 | glucose (0.4) | do (6.5) | 2.3 (2.5) | 575 (3.3) | 230 (1.2) | 5/5 | 5/5 |
| Control E | IID T-3 | — (—) | do not | 0.92 (1.0) | 178 (1.0) | 194 (1.0) | 5/5 | 4/5 |

(NOTE)
In all experiments yeast extract broth was used for the basal culture medium.

EXAMPLES 5, 6, 7

Cultivation was effected in quite the same way as in Example 1 except that the pH of the culture medium was held respectively at 5.0 (Control F), 6.0 (Example 5), 7.0 (Example 6) and 7.5 (Example 7) during the course of cultivation and Table 3 shows results obtained.

Indications are also made there of results of Control B of Example 1.

It follows from the results of Table 3 that the pH of the medium should preferably fall within the range of 6–7.

TABLE 3

| | | | | | | Conditions and Results | |
|---|---|---|---|---|---|---|---|
| | | | | | | Anti-tumor activity (Number of mice surviving / Number of mice tested) | |
| Experiments | Carbon source (concentration %) | PH control (PH) | Cell growth (OD$_{660}$) (ratio) | SLS-producing ability per unit culture medium (HU/ml) (ratio) | SLS-producing ability per unit cell concentration (HU/OD$_{660}$) (ratio) | After 20 days | After 30 days |
| Example 5 | glucose (0.4) | do (6.0) | 2.3 (2.6) | 455 (2.1) | 198 (0.8) | 5/5 | 5/5 |

TABLE 3-continued

| | | | | | | Anti-tumor activity | |
|---|---|---|---|---|---|---|---|
| | | | | SLS-producing ability per unit culture medium | SLS-producing ability per unit cell concentration | Number of mice surviving / Number of mice tested | |
| | Carbon source | PH | Cell growth | | | | |
| Experiments | (concentration %) | control (PH) | ($OD_{660}$) (ratio) | (HU/ml) (ratio) | ($HU/OD_{660}$) (ratio) | After 20 days | After 30 days |
| Example 6 | glucose (0.4) | do (7.0) | 2.4 (2.7) | 490 (2.3) | 204 (0.9) | 5/5 | 5/5 |
| Example 7 | glucose (0.4) | do (7.5) | 2.3 (2.6) | 414 (1.9) | 180 (0.8) | 4/5 | 3/5 |
| Control F | glucose (0.4) | do (5.0) | 1.2 (1.3) | <4 (<0.02) | <4 (<0.02) | 0/5 | 0/5 |
| Control B | — (—) | do not | 0.89 (1.0) | 214 (1.0) | 240 (1.0) | 5/5 | 5/5 |

(Note)
In all experiments St. pyogenes ATCC 21060 was used for the strain and yeast extract broth was used for the basal culture medium.

EXAMPLES 8, 9, 10, 11, 12

Table 4 shows results of cultivation which was conducted in the same way as in Example 1 except that the concentration of glucose added was set at 0.1% (Example 8), 0.3% (Example 9), 0.8% (Example 10), 2.0% (Example 11) and 5.0% (Example 12) and that cultivating time was 30 hours in Example 11 and 40 hours in Example 12. Results of Control B were indicated for comparison's sake. In either process of the present invention (Examples 8, 9, 10, 11, 12), as shown in Table 4, as compared to the conventional process (Control B), the cell growth increases 2-4 times as much, whereas the SLS-producing ability per unit cell concentration maintains an enough level and remarkable improvement is recognized in the total SLS-producing ability.

It is noted from the results of Table 4 that there should be a preferred range of amounts of glucose added in that the cell growth increases as the amount of glucose added increases, but on the contrary, the SLS-producing ability per unit cell concentration tends to be somewhat lowered.

EXAMPLES 13, 14, 15, 16

Results of Table 5 were obtained by cultivating in the same way as in Example 1 except that maltose (Example 13), mannose (Example 14), sucrose (Example 15) and lactose (Example 16) were used respectively in the amount of 0.4% instead of glucose as the fermentable carbon source.

Further, as their respective Controls G, H, I and J indications are made of results obtained by cultivating in the same way as in Control A, using the said carbon sources instead of glucose in Control A, together with the results of Control B not using the carbon source.

According to the process of the present invention, in the case of either carbon source, the cell growth increases markedly and in addition, there can be obtained bacterial cells excellent in the SLS-producing ability as well as in the anti-tumor activity. In the case, on the other hand, of adding the carbon source but not controlling the pH, true, the cell growth increases to some extent, but the SLS-producing ability and anti-tumor activity are markedly reduced or lost.

TABLE 4

| | | | | | | Anti-tumor activity | |
|---|---|---|---|---|---|---|---|
| | | | | SLS-producing ability per unit culture medium | SLS-producing ability per unit cell concentration | Number of mice surviving / Number of mice tested | |
| | Carbon source | PH | Cell growth | | | | |
| Experiments | (concentration %) | control (PH) | ($OD_{660}$) (ratio) | (HU/ml) (ratio) | ($HU/OD_{660}$) (ratio) | After 20 days | After 30 days |
| Example 8 | glucose (0.1) | do (6.5) | 1.6 (1.8) | 406 (1.9) | 254 (1.1) | 5/5 | 5/5 |
| Example 9 | glucose (0.3) | do (6.5) | 2.2 (2.5) | 545 (2.5) | 248 (1.0) | 5/5 | 5/5 |
| Example 10 | glucose (0.8) | do (6.5) | 2.5 (2.8) | 540 (2.5) | 216 (0.9) | 5/5 | 5/5 |
| Example 11 | glucose (2.0) | do (6.5) | 2.8 (3.1) | 504 (2.4) | 180 (0.8) | 5/5 | 5/5 |
| Example 12 | glucose (5.0) | do (6.5) | 3.9 (4.4) | 581 (2.7) | 149 (0.6) | 5/5 | 5/5 |
| Control B | — (—) | do not | 0.89 (1.0) | 214 (1.0) | 240 (1.0) | 5/5 | 5/5 |

(Note)
In all experiments St. pyogenes ATCC 21060 was used for the strain and yeast extract broth was used for the basal culture medium.

TABLE 5

Conditions and Results

| Experiments | Carbon source (concentration %) | PH control (PH) | Cell growth (OD$_{660}$) (ratio) | SLS-producing ability per unit culture medium (HU/ml) (ratio) | SLS-producing ability per unit cell concentration (HU/OD$_{660}$) (ratio) | Anti-tumor activity Number of mice surviving / Number of mice tested After 20 days | After 30 days |
|---|---|---|---|---|---|---|---|
| Example 13 | maltose (0.4) | do (6.5) | 2.6 (2.9) | 785 (3.7) | 302 (1.6) | 5/5 | 5/5 |
| Control G | maltose (0.4) | do not | 1.4 (1.6) | 210 (1.0) | 150 (0.6) | 3/5 | 2/5 |
| Example 14 | mannose (0.4) | do (6.5) | 2.2 (2.5) | 475 (2.2) | 216 (0.9) | 5/5 | 5/5 |
| Control H | mannose (0.4) | do not | 1.2 (1.3) | <4 (<0.02) | <4 (<0.02) | 1/5 | 0/5 |
| Example 15 | sucrose (0.4) | do (6.5) | 2.6 (2.9) | 624 (2.9) | 240 (1.0) | 5/5 | 5/5 |
| Control I | sucrose (0.4) | do not | 1.3 (1.5) | <4 (<0.02) | <4 (<0.02) | 0/5 | 0/5 |
| Example 16 | lactose (0.4) | do (6.5) | 2.3 (2.6) | 580 (2.7) | 252 (1.1) | 5/5 | 5/5 |
| Control J | lactose (0.4) | do not | 1.2 (1.3) | <4 (<0.02) | <4 (<0.02) | 0/5 | 0/5 |
| Control B | — (—) | do not | 0.89 (1.0) | 214 (1.0) | 240 (1.0) | 5/5 | 5/5 |

(Note)
In all experiments St. pyogenes ATCC 21060 was used for the strain and yeast extract broth was used for the basal culture medium.

EXAMPLES 17, 18

Results of Table 6 were obtained by cultivating in the same way as in Example 1 except that polypeptone broth [prepared by adjusting 1000 ml of aqueous solution containing 5 g of peptone (BBL), 5 g of yeast extract and 5 g of sodium chloride to pH 7.2–7.4 and sterilizing at 121° C. for 20 minutes] (Example 17) and soy peptone broth [prepared by adjusting 1000 ml of aqueous solution containing 30 g of phytone (BBL) to pH 7.2–7.4 and sterilizing at 121° C. for 20 minutes] (Example 18) were substituted for yeast extract of Example 1 as the basal culture medium.

Indications are also made of results obtained by cultivating in the same way as in Control B, using the polypeptone broth (Control K) and the soy peptone broth (Control L) instead of 5% yeast extract broth.

TABLE 6

Conditions and Results

| Experiments | Basal culture medium | Carbon source (concentration %) | PH control (PH) | Cell growth (OD$_{660}$) (ratio) | SLS-producing ability per unit culture medium (HU/ml) (ratio) | SLS-producing ability per unit cell concentration (HU/OD$_{660}$) (ratio) | Anti-tumor activity Number of mice surviving / Number of mice tested After 20 days | After 30 days |
|---|---|---|---|---|---|---|---|---|
| Example 17 | polypeptone broth | glucose (0.4) | do (6.5) | 2.3 (4.8) | 685 (5.4) | 298 (1.1) | 5/5 | 5/5 |
| Control K | polypeptone broth | — (—) | do not | 0.48 (1.0) | 126 (1.0) | 262 (1.0) | 5/5 | 4/5 |
| Example 18 | soy* peptone broth | glucose (0.4) | do (6.5) | 2.4 (2.5) | 643 (40.1) | 268 (16.8) | 5/5 | 5/5 |
| Control L | soy* peptone broth | — (—) | do not | 0.96 (1.0) | 16 (1.0) | 16 (1.0) | 1/5 | 0/5 |

(Note)
(i)*This soy peptone broth contains about 0.4% reducing sugar.
(ii)In all experiments St. pyogenes ATCC 21060 was used for the strain.

In the case of polypeptone broth and soy peptone broth, according to the process of the present invention the cell growth increases 4.8 times and 2.5 times that of the no glucose-added statical cultivation (Controls K and L) respectively and the SLS-producing ability and anti-tumor activity as well were better.

In Control L, the SLS-producing ability is lowered despite the fact that no glucose was added, and fermentable sugar primarily contained abundantly in the soy peptone is considered to be responsible for this.

EXAMPLE 19

Results of Table 7 below were obtained by cultivating in the same way as in Example 18 except that no glucose was added to the same soy peptone as used in Example 18.

Results of Control L were indicated for comparison's sake.

preparations showed that all of the mice tested (one group consisting of 5 mice) survived 30 days after intraperitoneal inoculation of Ehrlich ascites carcinoma.

What we claim is:

TABLE 7

| | | Conditions and Results | | | | | Anti-tumor activity | |
|---|---|---|---|---|---|---|---|---|
| | | | | | SLS-producing ability per unit culture medium | SLS-producing ability per unit cell concentration | Number of mice surviving / Number of mice tested | |
| Experiments | Basal culture medium | Carbon source (concentration %) | PH control (PH) | Cell growth ($OD_{660}$) (ratio) | (HU/ml) (ratio) | ($HU/OD_{660}$) (ratio) | After 20 days | After 30 days |
| Example 19 | soy* peptone broth | — (—) | do (6.5) | 1.2 (1.3) | 312 (19.5) | 260 (16.3) | 5/5 | 5/5 |
| Control L | soy* peptone broth | — (—) | do not | 0.96 (1.0) | 16 (1.0) | 16 (1.0) | 1/5 | 0/5 |

(Note)
(i)*This soy peptone broth contains about 0.4% reducing sugar.
(ii) In both experiments St. pyogenes ATCC 21060 was used for the strain.

It is noted from the results of Table 7 that in the case of basal culture medium primarly containing fermentable carbon sources, cells high in SLS-producing ability and in anti-tumor activity can be obtained in good yield by only controlling the pH of the culture medium.

Comparison between Example 19 and Example 18 hereinbefore mentioned shows that better results can be obtained by further addition of glucose even in such a case as in using basal culture medium primarly containing fermentable carbon sources.

EXAMPLE 20

500 ml of 10% yeast extract broth (prepared by dissolving 100 g of yeast extract in 500 ml of distilled water, adjusting to pH 7.2-7.4 then boiling at 100° C. for 1 hour, cooling in water, then filtering for removal of precipitates, once again boiling at 100° C. for 30 minutes after readjustment of pH to 7.2-7.4, cooling in water and filtering, followed by measuring up to 1000 ml in a flask) and 500 ml of 300 mM phosphate buffer solution (pH 7.3) were mixed together and sterilized at 121° C. for 20 minutes. To this mixture was added sterilized glucose solution in such a manner as to finally reach 0.4% in glucose content based on the total amount of the culture solution and was inoculated with 50 ml (5% V/V) of culture solution of St. pyogenes ATCC 21060 cultivated in advance in the nutrient broth and then it was subjected to statical cultivation at 37° C. for 20 hours. By the instant cultivation bacterial multiplication with $OD_{660}$ of 2.2 was observed and it is about 2.5 times as much as that obtained by conventional statical cultivation ($OD_{660}$=0.89, Control B).

The SLS-producing ability (HU/ml) per unit culture solution and SLS-producing ability (HU/ml) per unit cell concentration indicated as high values as 466 and 212, respectively, and results obtained by conducting the in vivo anti-tumor activity tests on the lyophilized 1. In a process for the cultivation of Streptococcus pyogenes which comprises cultivating Streptococcus pyogenes in a culture medium for multiplication of bacterial cells having an anti-tumor activity, the improvement wherein
(A) the culture medium used contains fermentable carbon sources in an amount of 0.3 to 5% of the culture medium and
(B) the pH of the culture medium is maintained in the range of 6 to 7.5 during the course of cultivation.

2. A process for cultivation according to claim 1 in which the fermentable carbon sources are contained in the amount of 0.3 to 2% in the culture medium.

3. A process for cultivation according to claim 1 in which the culture medium is held at a pH in the range of 6 to 7 during the course of cultivation.

4. A process for cultivation according to claim 1 in which the fermentable carbon sources are fermentable saccharides.

5. A process for cultivation according to claim 4 in which the fermentable saccharides are fermentable monosaccharides or disaccharides.

6. A process for cultivation according to claim 4 in which the fermentable monosaccharides are glucose.

7. A process for cultivation according to claim 4 in which the fermentable disaccharides are sucrose.

8. A process for cultivation according to claim 1, which comprises using, as the culture medium, those which are prepared by adding fermentable carbon sources in the amount of 0.3 to 2% to yeast extract broth.

9. A process for cultivation according to claim 1, which comprises using, as the culture medium, those which are prepared by adding fermentable carbon sources in the amount of 0.3 to 1.5% to soy peptone broth.

* * * * *